United States Patent [19]

Fleet

[11] Patent Number: 4,861,892

[45] Date of Patent: Aug. 29, 1989

[54] METHOD FOR SYNTHESIS OF DEOXYMANNOJIRIMYCIN

[75] Inventor: George W. J. Fleet, Oxford, United Kingdom

[73] Assignee: G. D. Searle & Co., Skokie, Ill.

[21] Appl. No.: 249,153

[22] Filed: Sep. 26, 1988

Related U.S. Application Data

[63] Continuation-in-part of Ser. No. 155,667, Feb. 12, 1988, abandoned.

[51] Int. Cl.$^4$ .................. A61K 31/445; C07D 211/42
[52] U.S. Cl. ...................................... 546/219; 546/214; 546/14
[58] Field of Search .................. 546/219, 14; 549/214

[56] References Cited

PUBLICATIONS

Legler and Julich, Carbohyd. Res. 128, 61–72 (1984).
Fleet and Smith, Tetrahedron Lett. 26(11), 1469–1472 (1985).
Fleet et al., Tetrahedron Lett. 25(36), 4029–4032 (1984).
Fleet et al., Tetrahedron 43(5), 979–990 (1987).
Leontine et al., Chem. Absts. 98; 72630 (1983).
Hulyalkar and Jones, Can. J. Chem. 41, 1898–1904 (1963).
Niwa et al., J. Antibiotics XXXVII(12), 1579'1586 (1984).
Iida et al., "J. Org. Chem.", (1987) vol. 52, pp. 3337–3342.

Primary Examiner—Robert T. Bond
Attorney, Agent, or Firm—Scott J. Meyer; James W. Williams, Jr.

[57] ABSTRACT

A method is disclosed for the chemical synthesis of 1,5-dideoxy-1,5-imino-D-mannitol or 1,5-dideoxy-1,5-imino-L-mannitol from, respectively, 2,3-O-isopropylidene-L-gluono-γ-lactone or 2,3-O-isopropylidene-D-gulono-γ-lactone which comprises carrying out interconversion between the L-gulono and D-mannono forms or between the D-gulono and L-mannono forms, respectively, and connecting of C-1 to C-5 by nitrogen.

18 Claims, No Drawings

METHOD FOR SYNTHESIS OF DEOXYMANNOJIRIMYCIN

CROSS-REFERENCE TO RELATED APPLICATION

This is a continuation-in-part of copending application Ser. No. 155,667, filed Feb. 12, 1988, now abandoned.

BACKGROUND OF THE INVENTION

This invention relates to a novel method for the chemical synthesis of 1,5-dideoxy-1,5-imino-D-mannitol and the corresponding L-mannitol derivative.

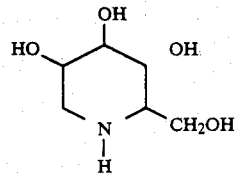

1,5-Dideoxy-1,5-imino-D-mannitol

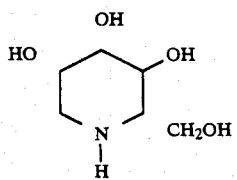

1,5-Dideoxy-1,5-imino-L-mannitol

In order to show stereoisomerism, solid and dotted lines show bonds directed above or below, respectively, the plane of the paper.

1,5-Dideoxy-1,5-imino-D-mannitol, also known as deoxymannojirimycin, is a potent mannosidase inhibitor. It is also useful in the production of inhibitors of the human immuno-deficiency virus as described in co-pending applications Ser. Nos. 136,219 and 136,224, both filed Dec. 21, 1987.

The conventional synthesis of 1,5-dideoxy-1,5-imino-D-mannitol and the corresponding L-gulo derivative is described by Legler and Jülish, Carbohydr. Res. 128, 61–72 (1984). They carried out the synthesis in essentially 7 steps from 2,3:5,6-di-O-isopropylidene-α-D-mannofuranose, which can be described briefly as follows:

A. Reaction of 2,3:5,6-di-O-isoproylidene-α-D-mannofuranose with benzyl chloride to produce benzyl 2,3:5,6-di-O-isopropylidene-E-D-mannofuranoside (1).

B. Selective removal of the 5,6-isopropylidene protecting group from compound (1) by HCl in methanol to give the benzyl 2,3-O-isopropylidene-α-D-mannofuranoside (2).

C. Reaction of compound (2) with trityl chloride in pyridine to provide benzyl 2,3-O-isopropylidene-6-O-trityl-α-D-mannofuraoside (3).

D. Oxidation of compound (3) with methyl sulfoxide-acetic anhydride to produce as a main product the ketone benzyl 2,3-O-isopropylidene-6-O-trityl-α-D-lyxo-hexofuranoside-5-ulose (4) and a by-product (5) identified as the 5-O-methylthiomethyl derivative of compound (3).

E. Conversion of the ketone compound (4) into the oxime and reduction with Raney nickel to give a mixture of compound (6a) having the D-manno configuration, namely benzyl 5-amino-5-deoxy-2,3-O-isoproylidene-6-O-trityl-α-D-mannofuranoside, and compound (6b) having the L-gulo configuration, namely, the corresponding -α-L-gulofuranoside.

F. Trityl cleavage of compounds (6a) and (6b) with HCl in methanol to provide benzyl 5-amino-5-deoxy-2,3-O-isopropylidene-α-D-mannofuranoside (7a) and the corresponding -α-L-gulofuranoside (7b).

G. Deprotection of compound 7a and rearrangement to the desired six-membered cyclic derivative was carried out as follows: Reductive debenzylation of compound (7a) by hydrogenation using a catalyst prepared from palladium hydroxide on charcoal followed by cleavage of the isopropylidene group with HCl to yield 1,5-dideoxy-1,5-imino-D-mannitol (12a). Corresponding hydrogenation of compound (7b) gave 1,5-dideoxy-1,5-imino-L-gulitol (12b).

The enantiospecific synthesis of D-deoxymannojirimycin from D-glucose is described by Fleet and Smith, Tetrahedron Lett. 26, 1469–1472 (1985). According to this synthesis, D-glucose is converted to the azidomannofuranoside which is then cyclised by intramolecular nucleophilic attack on C-6 to the bicyclic amine in which the original C-5 hydroxyl of glucose is unprotected. That is, the formation of the piperidine ring is achieved by intramolecular nucleophilic displacement of a leaving group at C-6 by an amino group at C-2. Thus, the primary hydroxyl group in the azidodiol was selectively tosylated and the sulfonate ester was hydrogenated in the presence of palladium black. The resulting amine was treated with sodium acetate in ethanol, and subsequently with benzyl chloroformate, to give the bicyclic benzyl carbonate. Hydrolysis of the acetal function in the latter compound by aqueous trifluoroacetic acid, followed by reduction with sodium borohydride gave

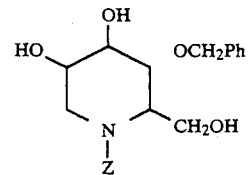

Removal of the benzyl (OCH$_2$Ph) and benzyloxycarbonyl (Z) protecting groups by hydrogenolysis with palladium hydroxide catalyst gave D-deoxymannojirimycin.

Other such lengthy stepwise syntheses of D-deoxymannojirimycin from D-mannose or D-glucose and their derivatives are described by Fleet et al., Tetrahedron Lett. 25, 4029–4032 (1984); Fleet et al., Tetrahedron 43, 979–990 (1987); and Leontein et al., Acta Chem. Scand. Ser. B, B36(8), 515–518 (1982).

While the foregoing methods for the production of D-deoxymannojirimycin are useful, synthesis of the desired compound in fewer steps and in substantial yield would be of significant value.

DESCRIPTION OF THE INVENTION

In accordance with the present invention a novel method for the chemical synthesis of 1,5-dideoxy-1,5-imino-D-mannitol (D-deoxymannojirimycin) and the corresponding L-mannitol stereoisomer (L-deoxymannojirimycin) is provided. The method comprises a convenient interconversion between the L-gulono and D-mannono forms or between the D-gulono and L-mannono forms, respectively, in which the deoxymannojirimycin is prepared in fewer steps than described by Legler and Jülish, supra, from a corresponding 2,3-O-isopropylidene or 2,3:,5,6-di-O-isopropylidene protected sugar starting material. The method also involves a novel connecting of C-1 to C-5 by nitrogen.

According to one embodiment of the invention, deoxymannojirimycin (DMJ) and D-mannonolactam are synthesized by a series of steps in which the piperidine ring is derived by introducing azide with inversion of configuration at C-5 of L-gulonolactone in which the hydroxyl groups at C-2, C-3 and C-6 are protected, the resulting azidolactone is reduced which leads to the formation of the δ-lactam, the resulting lactam is reduced to form the corresponding amine and all the protecting groups are removed to give the desired DMJ. Hydrolysis of the lactam gives the mannonolactam.

According to another embodiment of the invention, L-deoxymannojirimycin and L-mannonolactam are similarly synthesized by a corresponding series of steps from the D-gulonolactone configuration.

In a preferred embodiment of the invention the L-deoxymannojirimycin is chemically synthesized from the known compound 2,3-O-isopropylidene-D-gulono-γ-lactone by a series of steps comprising:

(a) introducing a silyl protecting group at C-6, (b) esterifying the alcohol at C-5 with triflic anhydride to give the triflate ester and then introducing the azide group at C-5, (c) reducing the azide group with a hydrogenation catalyst to provide a cyclic secondary amine, (d) reducing said amine with a borane reducing agent followed by deprotecting the resulting product by acid hydrolysis to remove the isopropylidene and silyl groups and thereby yield L-deoxymannojirimycin.

In another preferred embodiment of the invention the corresponding D-deoxymannojirimycin is chemically synthesized from 2,3-O-isopropylidene-L-gulono-γ-lactone by a similar series of steps.

Preferred reactants for use in the various steps of the foregoing syntheses are:

(a) introducing the silyl protecting group by reaction with t-butyldimethylsilyl chloride;

(b) esterification in the presence of pyridine and dichloromethane and introduction of the azide group by treatment of the triflate ester with sodium azide;

(c) reduction by palladium catalyzed hydrogenation, e.g. hydrogenation with 10% palladium on carbon;

(d) reduction with borane-methyl sulfide complex, $(CH_3)_2S-BH_3$, followed by hydrolysis with aqueous trifluoroacetic acid.

Other such suitable reactants for use in the foregoing syntheses will be apparent to the person skilled in the art after reading the present disclosure. These reactants are used in proportions such as to satisfy the stoichiometry of the above reaction steps. Illustrative of such other reacants are the use of t-butylidphenylsilyl chloride to introduce the silyl protecting group, introduction of the azide group with potassium azide, reduction with amine boranes, hydrolysis with HCl to cleave protecting groups and the use of other solvent media such as DMF, THF and the like.

The 2,3-O-isopropylidene protected starting materials can be prepared by methods analogous to those known in the art such as described, e.g., by Hulyalkar and Jones, *Can. J. Chem.* 41, 1898–1904 (1963). Thus 2,3-O-isopropylidene-D-gulono-γ-lactone can be prepared from 2,3:5,6-di-O-isopropylidene-D-gulono-γ-lactone by a deprotection reaction to selectively cleave the 5,6-isopropylidene protecting group. The deprotection can be carried out, for example, by acid cleavage such as with acetic acid. The known compound 2,3:5,6-di-O-isopropylidene-D-gulono-γ-lactone can be prepared from the commercially available D-gulono-γ-lactone by introduction of the 2,3-isopropylidene and 5,6-isopropylidene protecting groups. These protecting groups can be introduced by the p-toluenesulfonic acid catalyzed reaction of the D-gulono-γ-lactone with acetone and 2,2-dimethoxypropane. It will be understood that other protecting groups can be used in these starting materials in place of the isopropylidene groups, e.g., the cyclohexylidene group. Rearrangement of the azidolactone to the lactam can proceed in a manner somewhat analogous to the formation of δ-lactams from 5-azido-5-deoxy-1,4-lactones as described by Paulson and Todt, *Angew. Chem. Internat. Ed.* 5, 495 (1966).

In these various embodiments of the invention to chemically synthesize the L-deoxymannojirimycin, the overall process including intermediate products can be illustrated by the following series of steps:

A. Starting with 2,3-O-isopropylidene-D-gulono-γ-lactone, introduce a silyl protecting group at C-6 to provide the 6-O-tert-butyldimethylsilyl-2,3-O-isopropylidene-D-gulono-γ-lactone.

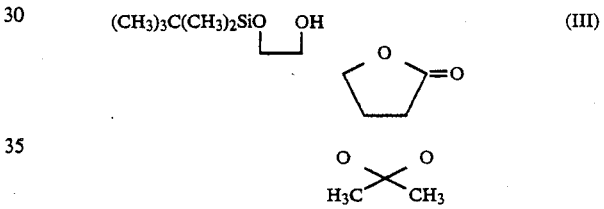

B. Carry out esterification of the alcohol with triflic anhydride to give the triflate ester at C-5 and then introduce the azide group to give the azido derivative 5-azido-6-O-tert-butyldimethylsilyl-5-deoxy-2,3-O-isopropylidene-L-mannono-γ-lactone.

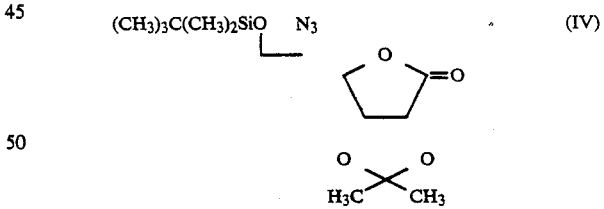

C. Provide for reduction of the azide by palladium catalyzed hydrogenation to produce the cyclic secondary amine 6-O-tert-butyldimethylsilyl-1,5-dideoxy-1,5-imino-2,3-O-isopropylidene-L-mannonic-δ-lactone.

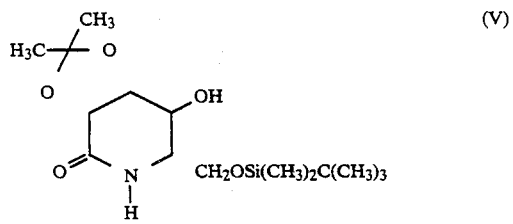

D. Carry out the reduction of the amine with borane-methyl sulfide complex followed by hydrolysis with aqueous trifluoroacetic acid to remove the isopropylidene group and the silyl group and thereby yield the desired L-deoxymannojirimycin, II.

The L-deoxymannojirimycin is a novel compound as are the other final products prepared in steps A, B, C and D, above. The cyclized amine prepared in step C also can be used to prepare the novel compoound 1,5-dideoxy-1,5-imino-L-mannonic-δ-lactam by acid hydrolysis to remove the protecting groups as in step D, above.

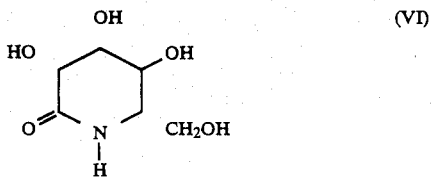

(VI)

The corresponding 1,5-dideoxy-1,5-imino-D-mannonic-δ-lactam is a known enzyme inhibitor.

The δ-lactam prepared in step C, above, and its enantiomer are also useful as intermediates in the synthesis of stereoisomers of castanospermine. See Fleet et al., *Tetrahedron Lett.* 29, 3603–3606 (1988).

The following detailed examples will further illustrate the invention although it will be understood that the invention is not limited to these specific examples.

EXAMPLE 1

A. 2,3:5,6-Di-O-isopropylidene-D-gulono-γ-lactone

D-Gulono-γ-lactone (15.47 g, 86.9 mmol) was stirred with acetone (160 ml), 2,2 dimethoxypropane (40 ml) and a catalytic amount of para-toluene-sulphonic acid under dry nitrogen for 36 hr when thin layer chromatography (t.l.c.) (ethyl acetate) revealed no starting material $R_f$ 0.0 and one product $R_f$ 0.9. The reaction mixture was stirred with an excess of sodium bicarbonate and the solvent removed under reduced pressure. The residue was dissolved in dichloromethane (200 ml) and washed with water (3×200 ml). The organic extracts were dried (MgSO$_4$) and the solvent removed under reduced pressure to give a white crystalline solid which was recrystallized from ethyl acetate to yield the title compound (18.38 g, 82%) as a white crystalline solid. M.p. 151°–153° C. (lit 152°–153° C.). $[\alpha]_D^{20}$ −70° (c 1 in acetone) (lit. −64° (c 2.8 in acetone)). $^{13}$C NMR (CDCl$_3$); 173.3 (s, C-1), 114.7 (s), 110.5 (s), 80.9, 76.0, 75.7 and 75.2 (4×d, C-2, C-3, C-4 and C-5), 65.1 (d, C-6), 26.5 (q), 25.7 (q), 25.0 (q).

B. 2,3-O-Isopropylidene-D-gulono-γ-lactone 2,3:5,6-di-O-Isopropylidene-D-gulono-γ-lactone (18.25 g, 70.7 mmol) was dissolved in acetic acid/water (7:1, 200 ml) and stirred at 30° C. for 16 hr when t.l.c. (ethyl acetate/hexane 1:1) revealed no starting material $R_f$ 0.5 and one major produce $R_f$ 0.1. The solvent was removed under reduced pressure to give a yellow oil. Trituration with benzene (50 ml) gave a solid which was shaken with ethyl acetate/acetone (1:1, 250 ml). The resulting suspension was filtered and solvents removed under reduced pressure to yield an amorphous yellow solid which was recrystallized from ethyl acetate to yield the title compound (12.18 g, 79%) M.p. 139°–141° C. $[\alpha]_D$ −79.4° (c 1 in acetone) (lit. m.p. 142°–143° C., $[\alpha]_D^{20}$ −76.5° (c 2.8 in acetone)).

C. 6-O-tert-Butyldimethylsilyl-2,3-O-isopropylidene-D-gulono-γ-lactone 2,3-O-Isopropylidene-D-gulono-γ-lactone (8.03 g, 36.8 mmol) was stirred in dry dimethylformamide (DMF) (75 ml) and the solution cooled to −40° C. under dry nitrogen. Imidazole (3.75 g, 55.2 mmol) and tert-butyldimethylsilyl chloride (6.10 g, 40.5 mmol) were added. The reaction was stirred at −40° C. for 2 hr when t.l.c. (ethyl acetate/hexane 1:1) revealed no starting material $R_f$ 0.1 and one major product $R_f$ 0.8. The solvent was removed under reduced pressure, the residue was dissolved in brine (200 ml) and extracted with dichloromethane (3×200 ml). The organic extracts were dried (MgSO$_4$) and the solvent removed under reduced pressure to give a colorless oil. Purification by flash column chromatography (ethyl acetate/hexane 1:3) gave the title compound as a colorless oil (8.67 g, 71%), $[\alpha]_D^{20}$ −46.5° (c, 0.5 in CHCl$_3$), m/z (C.I. NH$_3$); 350 (M+NH$_4^+$, 100%). $^1$H NMR, (CDCl$_3$); 4.85 (2H, m), 4.58 (1H, dd), 4.07 (1H, m), 3.83 (2H, dd), 2.71 (1H, d, OH), 1.50 and 1.41 (2×3H, 2×s), 0.92 (9H, s), 0.11, (6H, s). $^{13}$C NMR (CDCl$_3$); 173.7 (s, C-1), 114.6 (s), 79.1, 76.4, 76.3 and 70.9 (4×d, C-2, C-3, C-4 and C-5), 63.1 (t, C-6), 26.65 (q), 25.7 (q), 25.6 (q), 18.1 (s), −5.6 (q).

D. 5-Azido-6-O-tert-butyldimethylsilyl-5-deoxy-2,3-O-isopropylidene-L-mannono-γ-lactone 6-O-tert-Butyldimethylsilyl-2,3-O-isopropylidene-D-gulono-γ-lactone (8.91 g, 26.8 mmol) was dissolved in dry dichloromethane (50 ml) and pyridine (6.46 ml, 80.1 mmol) was added. The reaction was cooled to −30° C. with stirring under dry nitrogen. Trifluoromethanesulphonic anhydride (9.28 ml, 55.3 mmol) was added and the reaction was stirred for 1 hr when t.l.c. (ethyl acetate/hexane 1:1) revealed no starting material $R_f$ 0.8 and one product $R_f$ 0.9. The reaction mixture was then diluted with dichloromethane (50 ml) and washed with aqueous HCl (2M, 100 ml) water and saturated sodium bicarbonate. The organic layer was dried (MgSO$_4$) and the solvent removed under reduced pressure to give crude 6-O-tert-butyldimethylsilyl-2,3-O-isopropylidene-5-O-trifluoromethanesulfonyl-D-gulonolactone, which without purification was dissolved in dry DMF (50 ml) and stirred under dry nitrogen with sodium azide (5.2 g, 80.4 mmol). After three hours t.l.c. (ethyl acetate/hexane 1:3) showed no starting material $R_f$ 0.4 and one product $R_f$ 0.5. The solvent was removed under reduced pressure and the residue dissolved in brine (100 ml), extracted with dichloromethane (3×100 ml); the organic extracts were combined, dried (MgSO$_4$) and the solvents removed under reduced pressure to give a crude yellow oil. Elution through a silica plug (ethyl acetate/hexane, 1:3) gave a colorless oil which crystallized on standing, to afford, after recrystallization from hexane, the title compound, (6.89 g, 72%) m.p. 86°–87°, $[\alpha]_D^{20}$ +8.6° (c 1.1 in CHCl$_3$). $\nu_{max}$ (CHCl$_3$); 2100 cm$^{-1}$ (N$_3$), 1760 cm$^{-1}$ (C=O).m/z (D.C.I. NH$_3$); 347 (M+NH$_4^+$, 319 (M+NH$_4$−N$_2^+$). $^1$H NMR (CDCl$_3$); 4.8 (2H, m H-2 and H-3, J$_{2,3}$ 5.18 Hz), 4.40 (1H, dd, H-4, J$_{3,4}$ 3.25 Hz), 4.06 (1H, dd, H-6', J$_{6,6'}$ 10.81 Hz, J$_{6',5}$ 5.43 Hz), 3.87 (1H, dd, H-6, J$_{6,5}$ 2.32 Hz), 3.75 (1H, ddd, H-5, J$_{5,4}$ 10.02 Hz), 1.50 and 1.45 (2×3H, 2×s), 0.93 (9H, s), 0.12 (6H, s). $^{13}$C NMR (CDCl$_3$); 174.4 (s, C-1), 114.4 (s), 76.4, 75.9 and 75.4 (3×d, C-2, C-3 and C-4), 63.1 (t, C-6), 60.4 (d, C-5), 26.8 (q), 26.0 (q), 25.7 (g), 18.2 (s), −5.6 (q). (Found: C, 50.42; H, 7.72; N, 12.05%. C$_{15}$H$_{27}$O$_5$N$_3$Si requires C, 50.42; H, 7.56; N, 11.76%).

E.
6-O-tert-Butyldimethylsilyl-1,5-dideoxy-1,5-imino-2,3-O-isopropylidene-L-mannonic-δ-lactam 5-Azido-6-O-tert-butyldimethylsilyl-5-deoxy-2,3-O-isopropylidene-L-mannono-γ-lactone (5.91 g, 16.6 mmol) was dissolved in methanol (25 ml) and stirred under hydrogen with a catalytic amount of 10% palladium on carbon for 14 hr when t.l.c. (ethyl acetate/hexane 1:3) revealed baseline material only and t.l.c. (10% methanol in dichloromethane) showed one major product R$_f$ 0.5. The reaction mixture was filtered through a cellite plug which was washed with methanol (3×10 ml). Solvents were removed under reduced pressure to give a colorless oil, which after purification by flash column chromatography (ethyl acetate) yielded the title compound (4.14 g, 76%), M.p. 104°–105° C. (Found: C, 54.58; H, 8.39; N, 4.16. C$_{15}$H$_{29}$O$_5$N requires C, 54.38; H, 8.76; N, 4.23%). [α]$_D^{20}$−17.91 (c 0.86 in CHCl$_3$). ν$_{max}$ (CHCl$_3$); 3300 cm$^{-1}$ (br, OH and NH). 1670 cm$^{-1}$ (C=O). m/z (A.C.E. NH$_3$ C.I.); 332 (m+H$^+$), 274 (m+H—CH$_3$COCH$_3$$^+$). $^1$H NMR (CDCl$_3$); 6.18 (br, NH), 4.63 (1H, d, H-2), 4.30 (1H, dd, H-3), 4.00 (1H, dd, H-6′), 3.59 (2H, m, H-6 and H-4), 3.37 (1H, m, H-5), 1.52 and 1.41 (2×3H, 2×s), 0.89, (9H, s), 0.09 ( 6H, s). $^{13}$C NMR (CDCl$_3$); 168.6 (s, C-1), 110.8 (s), 78.8, 72.8 and 70.8 (3×d, C-2, C-3 and C-4), 63.3 (t, C-6), 54.7 (d, C-5), 26.9 (q), 24.8 (q), 25.6 (q), 17.95 (s), −5.7 (q).

F. L-Deoxymannojirimycin

6-O-tert-Butyldimethylsilyl-1,5-dideoxy-1,5-imino-2,3-O-isopropylidene-L-mannonic-δ-lactam (100 mg, 0.3 mmol) was dissolved in dry tetrahydrofuran (THF) and stirred with borane:dimethylsulphide complex (90 μl, 0.9 mmol) under dry nitrogen for 4 hr when t.l.c. (ethyl acetate) showed no starting material R$_f$ 0.5 and one major product R$_f$ 0.9. The reaction was quenched with saturated sodium sulphate and the two phases separated. The aqueous phase was extracted with dichloromethane (3×5 ml), the organic phases were combined, dried (MgSO$_4$) and the solvent removed under reduced pressure.

The residue was dissolved in trifluoroacetic acid/water (1:1, 5 ml) and left to stand for 2 h when t.l.c. (ethanol/chloroform/ammonia, 45/45/10) revealed one product (R$_f$ 0.1). The solvent was removed under reduced pressure, and toluene (3×5 ml) was distilled from the residue. The product was purified by ion exchange chromatography to yield the title compound as a colorless oil. Treatment with aqueous hydrochloric acid (0.5M) and further purification by recrystallization from methanol yielded the title compound, as the hydrochloride salt, (41 mg, 72%), m.p. 185°–187° C., [α]$_D^{20}$+10.2° (c, 0.37 in water). m/z (CI NH$_3$); 164 (M+H$^+$, 100%), 128, 110. δ$_H$ (D$_2$O), 4.10 (1H, ddd, H2), 3.72 (1H, dd, H4), 3.69 (1H, dd, H6), 3.54 (1H, dd, H3), 3.27 (1H, dd, H1′), 3.10 (1H, dd, H1), 3.01 (1H, ddd, H5). δ$_C$ (D$_2$O); 73.1 (d, C2), 66.6 (d), 66.5 (d), 61.1 (d, C5), 58.8 (t, C6), 48.3 (t, C1).

G. 1,5-Dideoxy-1,5-imino-L-mannonic-δ-lactam

6-O-tert-Butyldimethylsilyl-1,5-dideoxy-1,5-imino-2,3-O-isopropylidene-L-mannonic-δ-lactam (66 mg, 0.2 mmol) was dissolved in trifluoroacetic acid/water (1:1, 5 ml) and left to stand for 1 hr when t.l.c. (10% methanol in chloroform) revealed no starting material R$_f$ 0.5 and t.l.c. (2:1 chloroform/methanol) revealed one product R$_f$ 0.5. The solvent was removed under reduced pressure and toluene (3×5 ml) was distilled from the residue. Trituration with ether gave a white crystalline solid which was recrystallized from methanol to give the title compound, (32 mg, 91%), m.p. 165°–170° C., [α]$_D^{20}$ −2.0° (C, 1.0 in water). m/z (DCI NH$_2$); 178 (M+H$^+$, 100%), 112. δ$_H$ (D$_2$O); 4.16 (1H, d, H2), 3.83 (1H, dd, H3), 3.68 (1H, dd, H4), 3.54 (2H, m, H6 and H6′), 3.19 (1H, m, H5). δ$_C$ (D$_2$O); 173.5 (s, Cl), 71.9 (d, C3), 68.2 (d, C2), 67.1 (d, C4), 61.1 (t, C6), 57.3 (d, C5).

EXAMPLE 2

Example 1 was repeated except that L-gulono-γ-lactone was used as the starting material in place of D-gulono-γ-lactone. Substantially similar results were obtained as in Example 1 to produce the following stereoisomeric products:

A. 2,3:5,6-Di-O-isopropylidene-L-gulono-γ-lactone.
B. 2,3-O-Isopropylidene-L-gulono-γ-lactone.
C. 6-O-tert-Butyldimethylsilyl-2,3-O-isopropylidene-L-gulono-γ-lactone.
D. 5-Azido-6-O-tert-butyldimethylsilyl-5-deoxy-2,3-O-isopropylidene-D-mannono-γ-lactone.
E. 6-O-tert-Butyldimethylsilyl-1,5-dideoxy-1,5-imino-2,3-O-isopropylidene-D-mannonic-δ-lactam.
F. D-Deoxymannojirimycin.
G. 1,5-Dideoxy-1,5-imino-D-mannonic-δ-lactam.

The latter compound is a known enzyme inhibitor. Niwa et al., *J. Antibiotics* 37 (12), 1579 (1984).

The specific synthesis of compounds A through G, above, was as follows:

A. 2,3:5,6-Di-O-isopropylidene-L-gulonolactone

L-Gulonolactone (20.00 g, 112.3 mmol) was stirred with acetone (160 ml), 2,2-dimethoxypropane (40 ml) and a catalytic amount of p-toluenesulphonic acid under dry nitrogen for 36 h when t.l.c. (ethyl acetate) revealed no starting material (R$_f$ 0.0) and one product (R$_f$ 0.9). The reaction mixture was stirred with an excess of sodium bicarbonate and the solvent removed under reduced pressure. The residue was dissolved in dichloromethane (200 ml) and washed with water (3×200 ml). The organic extracts were dried (magnesium sulphate) and the solvent removed under reduced pressure to give a solid which was recrystallized from ethyl acetate to yield 2,3:5,6-di-O-isopropylidene-L-gulonolactone, (22.89 g, 79%), m.p. 151°–153° C. [α]$_D^{20}$+68.4° (c, 1 in acetone) [lit. m.p. 153°–154° C. [α]$_D^{20}$+91.5°]. δ$_C$ (CDCl$_3$), 173.3 (s, C-1), 114.7 (s), 110.5 (s), 80.9, 76.0, 75.7 and 75.2 (4×d, C-2, C-3, C-4 and C-5), 65.1 (d, C-6), 26.5 (q), 25.7 (q), 25.0 (q).

B. 2,3-O-Isopropylidene-L-gulonolactone 2,3:5,6-Di-O-isopropylidene-L-gulonolactone (22.89 g, 88.7 mmol) was dissolved in acetic acid/water (7:1, 200 ml) and stirred at 30° C. for 16 h when t.l.c. (ethyl acetate/hexane 1:1) revealed no starting material (R$_f$ 0.5) and one major product (R$_f$ 0.1). The solvent was removed under reduced pressure to give a yellow oil. Trituration with benzene (50 ml) gave a solid which was shaken with ethyl acetate/acetone (1:1, 250 ml). The resulting suspension was filtered and solvents removed under reduced pressure to yield an amorphous yellow solid, which was recrystallized from ethyl acetate to yield 2,3-O-isopropylidene-L-gulonolactone, (14.31 g, 79%) as a white crystalline solid, m.p. 139°-141° C., $[\alpha]_D^{20}+76.2°$ (C, 1 in acetone).

C.
6-O-tert-Butyldimethylsilyl-2,3-O-isopropylidene-L-gulonolactone 2,3-O-Isopropylidene-L-gulonolactone (14.3 g, 65.6 mmol) was stirred in dry dimethylformamide (100 ml) and the solution cooled to −40° C. under dry nitrogen. Imidazole (6.86 g, 98.4 mmol) and tert-butyldimethylsilyl chloride (10.9 g, 72.2 mmol) were added. The reaction was stirred at −40° C. for 2 h when t.l.c. (ethyl acetate/hexane 1:1) revealed no starting material ($R_f$ 0.1) and one major product ($R_f$ 0.8). The solvent was removed under reduced pressure and the residue was dissolved in brine (200 ml) and extracted with dichloromethane (3×200 ml). The organic extracts were dried (magnesium sulphate) and the solvent removed under reduced pressure to give a colorless oil. Purification by flash column chromatography (ethyl acetate/hexane 1:3) gave 6-O-tert-butyldimethylsilyl-2,3-O-isopropylidene-L-gulonolactone, (15.44 g, 71%) as a colorless oil, $[\alpha]_D^{20}+51.6°$ (c, 0.64 in CHCl$_3$), m/z (CI NH$_3$); 350 (M+NH$_4^+$, 100%). $\delta_H$ (CDCl$_3$); 4.85 (2H, m), 4.58 (1H, dd), 4.07 (1H, m), 3.83 (2H, dd), 2.71 (1H, d, OH), 1.50 and 1.41 (2×3H, 2×s), 0.92 (9H, s), 0.11, (6H, s). $\delta_C$(CDCl$_3$); 173.7 (s, C-1), 114.6 (s), 79.1, 76.4, 76.3 and 70.9 (4×d, C-2, C-3, C-4 and C-5), 63.1 (t, C-6), 26.65 (q), 25.7 (q) 25.6 (q), 18.1 (s), −5.6 (a).

D.
5-Azido-6-O-tert-butyldimethylsilyl-5-deoxy-2,3-O-isopropylidene-D-mannolactone 6-O-tert-Butyldimethylsilyl-2,3-O-isopropylidene-L-gulonolactone (15.44 g, 46.4 mmol) was dissolved in dry dichloromethane (100 ml) and pyridine (11.19 ml, 138.8 mmol) was added. The reaction was cooled to −30° C. under dry nitrogen. Trifluoromethanesulphonic anhydride (16.1 ml, 95.8 mmol) was added and the reaction was stirred for 1 h when t.l.c. (ethyl acetate/hexane 1:1) revealed no starting material ($R_f$ 0.8) and one product ($R_f$ 0.9). The reaction mixture was then diluted with dichloromethane (100 ml) and washed with aqueous hydrochloric acid (2M, 100 ml aliquots), water and saturated sodium bicarbonate. The organic layer was dried (magnesium sulphate) and the solvent removed under reduced pressure to give the crude triflate which was dissolved in dry dimethylformamide (75 ml) and stirred under dry nitrogen with sodium azide (9.0 g, 139.3 mmol). After 3 h t.l.c. (ethyl acetate/hexane 1:3) showed no starting material ($R_f$ 0.4) and one product ($R_f$ 0.5). The solvent was removed under reduced pressure and the residue dissolved in brine (100 ml). This was extracted with dichloromethane (3×100 ml). The organic extracts were combined, dried (magnesium sulphate) and the solvents removed under reduced pressure to give a crude yellow oil. Elution through a silica plug (ethyl acetate/hexane 1:3) gave a colorless plug which crystallized on standing. Recrystallization from hexane yielded 5-azido-6-O-tert-butyldimethylsilyl-5-deoxy-2,3-O-isopropylidene-D-mannolactone, (12.6 g, 76%), m.p. 86°-87° C. $\nu_{max}$ (CHCl$_3$); 2100 (N$_3$), 1760 (C=O) cm$^{-1}$. m/z (DCI NH$_3$); 347 (M+NH$_4^+$), 319 (M+NH$_4$−N$_2^+$). $\delta_H$ (CDCl$_3$); 4.8 (2H, m, H-2 and H-3, $J_{2,3}$ 5.18 Hz), 4.40 (1H, dd, H-4, $J_{3,4}$ 3.25 Hz), 4.06 (1H, dd, H-6', $J_{6,6}$ 10.81 Hz, $J_{6',5}$ 5.43 Hz), 3.87 (1H, dd, H-6, $J_{6,5}$ 2.32 Hz), 3.75 (1H, ddd, H-5, $J_{5,4}$ 10.02 Hz), 1.50 and 1.45 (2×3H, 2s), 0.93 (9H, s), 0.12 (6H, s), $\delta_C$ (CDCl$_3$); 173.6 (s, C-1), 114.4 (s), 76.4, 75.9 and 75.4 (3d, C-2, C-3 and C-4), 63.1 (t, C-6), 60.4 (d, C-5), 26.8 (q), 26.0 (q), 25.7 (q), 18.2 (s), −5,6 (q). (Found: C, 50.42; H, 7.72; N, 12.05%. C$_{15}$H$_{27}$O$_5$N$_3$Si requires C, 50.42; H, 7.56; N, 11.76%). $[\alpha]_D^{20}-9.6°$ (c, 3 in CHCl$_3$).

E.
6-O-tert-Butyldimethylsilyl-2,3-O-isopropylidene-D-mannono-δ-lactam

5-Azido-6-O-tert-butyldimethylsilyl-5-deoxy-2,3-O-isopropylidene-D-mannolactone (11.69 g, 32.8 mmol) was dissolved in methanol (50 ml) and stirred under hydrogen with a catalytic amount of 10% palladium on carbon for 14 h when t.l.c. (ethyl acetate/hexane 1:3) revealed baseline material only and t.l.c. (10% methanol in dichloromethane) showed one major product ($R_f$ 0.5). The reaction mixture was filtered through a celite plug which was washed with filtered through a celite plug which was washed with methanol. Solvents were removed under reduced pressure to give a colorless oil. Purification by flash column chromatography (ethyl acetate) yielded 6-O-tert-butyldimethylsilyl-2,3-O-isopropylidene-D-mannono-δ-lactam, (9.88 g, 91%), as a white crystalline solid, m.p. 104°-105° C., $[\alpha]_D^{20}+19.2°$ (c, 1.02 in CHCl$_3$). $\nu_{max}$ (CHCl$_3$); 3300 cm$^{-1}$ (br, OH and NH), 1670 cm$^{-1}$ (C=O). m/z (A.C.E. NH$_3$ C.I.); 332 (M+H$^+$), 274 (M+H−CH$_3$COCH$_3^+$). $\delta_H$ (CDCl$_3$), 6.18 (br, NH), 4.63 (1H, d, H-2), 4.30 (1H, dd, H-3), 4.00 (1H, dd, H-6'), 3.59 (2H, m, H-6 and H-4), 3.37 (1H, m, H-5), 1.52 and 1.41 (2×3H, 2×s), 0.89, (9H, s), 0.09 (6H, s). $\delta_C$(CDCl$_3$); 168.6 (s, C-1), 110.8 (s), 78.8, 72.8 and 70.8 (3×d, C-2, C-3 and C-4), 63.3 (t, C-6), 54.7 (d, C-5), 26.9 (q), 24.8 (q), 25.6 (q), 17.95 (s), −5.7 (q). (Found: C, 54.19; H, 8.56; N, 4.26%. C$_{15}$H$_{29}$O$_5$N requires C, 54.38; H, 8.76; N, 4.23%).

F. Deoxymannojirimycin

6-O-tert-Butyldimethylsilyl-2,3-O-isopropylidene-D-mannono-δ-lactam (9.88 g, 29.6 mmol) was dissolved in dry tetrahydrofuran (50 ml) and stirred under dry nitrogen. Borane/dimethyl sulphide complex (10M, 8.89 ml) was added and the reaction was stirred for 2 h when t.l.c. (ethyl acetate) revaled no starting material ($R_f$ 0.5) and one product ($R_f$ 0.9). The reaction was quenched by cautious addition of methanol until effervescence had ceased. Solvents were removed under reduced pressure and methanol (3×50 ml) was distilled from the residue. The residue was dissolved in trifluoroacetic acid/water (2:1, 15 ml). The reaction was left to stand for 2 h when t.l.c. (ethyl acetate) revealed baseline material only. Solvents were removed under reduced pressure and toluene (3×20 ml) was distilled from the reaction mixture. The residue was purified by ion exchange chromatography to yield deoxymannojirimycin which was converted to its hydrochloride salt by treatment with aqueous hydrochloric acid (0.5M). This was further purified by recrystallization from ethanol to give deoxymannojirimycin hydrochloride, (4.50 g, 80%), m.p. 185°-186° C., $[\alpha]_D^{20}-15.3°$ (c, 0.50 in water), m/z (CI NH$_3$); 164 (M+H$^+$, 100%), 128, 110. $\delta_H$ (D$_2$O); 4.10 (1H, ddd, H2), 3.72 (1H, dd, H4), 3.69 (1H, dd, H6), 3.54 (1H, dd, H3), 3.27 (1H, dd, H1'), 3.10 (1H, dd, H1), 3.01 (1H, ddd, H5). $\delta_C$(D$_2$O); 73.1 (d, C2), 66.6 (d), 66.5 (d), 61.1 (d, C5), 58.8 (t, C6), 48.3 (t, C1).

G. D-Mannono-δ-lactam

6-O-tert-Butyldimethylsilyl-2,3-O-isopropylidene-D-mannono-δ-lactam (98 mg, 0.3 mmol) was dissolved in trifluoroacetic acid/water (1:1, 5 ml) and left to stand for 1 h when t.l.c. (10% methanol in chloroform) revealed no starting material ($R_f$ 0.5) and t.l.c. (2:1 chloroform/methanol) revealed one product ($R_f$ 0.5). The solvent was removed under reduced pressure and toluene (3×5 ml) was distilled from the residue. Trituration with ether gave a white crystalline solid which was recrystallized from methanol to give D-mannono-δ-lactam, (46 mg, 89%), m.p. 165°–169° C., $[\alpha]_D^{20}$ +0.9° (C, 1.0 in water) [lit. m.p. 168°–170° C., $[\alpha]_D^{20}$ −1.6° (c, 1.0 in water)]. m/z (DCI NH$_3$); 178 (M+H)+, 100%), 112. $\delta_H$ (D$_2$O); 4.16 (1H, d, H2), 3.83 (1H, dd, H3), 3.68 (1H, dd, H4), 3.54 (2H, m, H6 and H6'), 3.19 (1H, m, H5). $\delta_C$ (D$_2$O), 173.5 (s, C1), 71.9 (d, C3), 68.2 (d, C2), 67.1 (d, C4), 61.1 (t, C6), 57.3 (d, C5).

Various other examples will be apparent to the person skilled in the art after reading the present disclosure without departing from the spirit and scope of the invention. It is intended that all such other examples be included within the scope of the appended claims.

What is claimed is:

1. A method for the chemical synthesis of L-deoxymannojirimycin from 2,3-O-isopropylidene-D-gulono-γ-lactone comprising:
   (a) introducing a silyl protecting group at C-6,
   (b) esterifying the alcohol at C-5 with triflic anhydride to give the triflate ester and then introducing the azide group at C-5,
   (c) reducing the azide group with a hydrogenation catalyst to provide a cyclic secondary amine,
   (d) reducing said amine with a borane reducing agent followed by deprotecting the resulting product by acid hydrolysis to remove the isopropylidene and silyl groups and thereby yield L-deoxymannojirimycin.

2. The method of claim 1 in which the silyl protecting group is introduced by reaction of the 2,3-O-isopropylide-D-gulono-γ-lactone with t-butyldimethylsilyl chloride.

3. The method of claim 1 in which the esterification is carried out in the presence of pyridine and dichloromethane and the azide group is introduced by treatment of the triflate ester with sodium azide.

4. The method of claim 1 in which the azide reduction is carried out by hydrogenation in the presence of 10% palladium on carbon.

5. The method of claim 1 in which the amine reduction is carried out by reaction with borane-methyl sulfide complex followed by deprotecting by hydrolysis with aqueous trifluoroacetic acid.

6. The method of claim 1 in which the silyl protecting group is introduced by reaction of the 2,3-O-isopropylidene-D-gulono-γ-lactone with t-butyldimethylsilyl chloride, the esterification is carried out in the presence of pyridine and dichloromethane and the azide group is introduced by treatment of the triflate ester with sodium azide, the azide reduction is carried out by hydrogenation in the presence of 10% palladium on carbon, and the deprotecting is carried out by reaction with borane-methyl sulfide complex followed by deprotecting by hydrolysis with aqueous trifluoroacetic acid.

7. A method for the chemical synthesis of D-deoxymannojirimycin from 2,3-O-isopropylidene-L-gulono-γ-lactone comprising:
   (a) introducing a silyl protecting group at C-6,
   (b) esterifying the alcohol at C-5 with triflic anhydride to give the triflate ester and then introducing the azide group at C-5,
   (c) reducing the azide group with a hydrogenation catalyst to provide a cyclic secondary amine,
   (d) reducing said amine with a borane reducing agent followed by deprotecting the resulting product by acid hydrolysis to remove the isopropylidene and silyl groups and thereby yield D-deoxymannojirimycin.

8. The method of claim 7 in which the silyl protecting group is introduced by reaction of the 2,3-O-isopropylidene-L-gulono-γ-lactone with t-butyldimethylsilyl chloride.

9. The method of claim 7 in which the esterification is carried out in the presence of pyridine and dichloromethane and the azide group is introduced by treatment of the triflate ester with sodium azide.

10. The method of claim 7 in which the azide reduction is carried out by hydrogenation in the presence of 10% palladium on carbon.

11. The method of claim 7 in which the amine reduction is carried out by reaction with borane-methyl sulfide complex followed by deprotecting by hydrolysis with aqueous trifluoroacetic acid.

12. The method of claim 7 in which the silyl protecting group is introduced by reaction of the 2,3-O-isopropylidene-L-gulono-γ-lactone with t-butyldimethylsilyl chloride, the esterification is carried out in the presence of pyridine and dichloromethane and the azide group is introduced by treatment of the triflate ester with sodium azide, the azide reduction is carried out by hydrogenation in the presence of 10% palladium on carbon, and the deprotecting is carried out by reaction with borane-methyl sulfide complex followed by deprotecting by hydrolysis with aqueous trifluoroacetic acid.

13. The method of claim 1 or 7 including the additional step of preparing the initial 2,3-O-isopropylidene-D- or L-gulono-γ-lactone by a deprotecting reaction to selectively cleave the 5,6-isopropylidene protecting group from, respectively, 2,3:5,6-di-O-isopropylidene-D- or L-gulono-γ-lactone.

14. The method of claim 13 including the additional step of preparing the initial 2,3:5,6-di-O-isopropylidene-D- or L-gulono-γ-lactone from, respectively, D- or L-gulono-γ-lactone by introducing the 2,3-isopropylidene and 5,6-isopropylidene protecting groups.

15. 6-O-tert-Butyldimethylsilyl-2,3-O-isoproylidene-D-gulono-γ-lactone.

16. 5-Azido-6-O-tert-butyldimethylsilyl-5-deoxy-2,3-O-isopropylidene-L-mannono-γ-lactone.

17. 6-O-tert-Butyldimethylsilyl-1,5-dideoxy-1,5-imino-2,3-O-isopropylidene-L-mannonic-δ-lactam.

18. 1,5-Dideoxy-1,5-imino-L-mannonic-δ-lactam.

* * * * *

UNITED STATES PATENT AND TRADEMARK OFFICE
CERTIFICATE OF CORRECTION

PATENT NO. : 4,861,892
DATED : Aug. 29, 1989
INVENTOR(S) : GEORGE W. J. FLEET

It is certified that error appears in the above—identified patent and that said Letters Patent is hereby corrected as shown below:

In the structural chemical formulas at col. 1, lines 18, 27, 28 and 30; col. 2, line 41; col. 4, lines 32, 34, 47, 50, 63, 65; col. 5, lines 15, 16 and 18, dotted lines should be inserted in the blank spaces between the ring structures and the adjacent, dangling substituents to show bonds directed below the plane of the paper.

Signed and Sealed this

Eleventh Day of September, 1990

Attest:

HARRY F. MANBECK, JR.

Attesting Officer     Commissioner of Patents and Trademarks